United States Patent [19]

Markson

[11] Patent Number: 5,900,416
[45] Date of Patent: May 4, 1999

[54] AQUEOUS CAFFEINE DOSAGE FORMS

[75] Inventor: Stephen A. Markson, West Orange, N.J.

[73] Assignee: Anthea Enterprises Incorporated, Kenilworth, N.J.

[21] Appl. No.: 08/595,366

[22] Filed: Feb. 1, 1996

[51] Int. Cl.[6] .................................................. A01N 43/90
[52] U.S. Cl. .............................................................. 514/264
[58] Field of Search .............................................. 514/264

[56] References Cited

U.S. PATENT DOCUMENTS 4,076,856  2/1978  Zeitlin .

FOREIGN PATENT DOCUMENTS 2559384  7/1977  Germany .

OTHER PUBLICATIONS

CA 85: 130513, Klosa, Jul. 1, 1976.
CA 84: 49816, Klosa, Nov. 27, 1974.
Merck 10th edition, entries 6329 and 6366, 1983.
CA 107 :54012 Blass, 1977.
CA 81: 158677 Rice, 1974.
CA 87: 106752, Klossa, 1977.
WP 86–149191, Budnikou, 1985.
WP 82–13420E, Salvanova, 1981.

Primary Examiner—Rebecca Cook
Attorney, Agent, or Firm—Lerner, David, Littenberg, Krumholtz & Mentlik, LLP

[57] ABSTRACT

Aqueous caffeine solutions containing a co-solubilizing agent selected from niacinamide, nicotinic acid and mixtures thereof present at a level up to the maximum concentration soluble in water and in a weight ratio to caffeine less than 1.50:1, wherein the caffeine is present up to the maximum level between about 2 and about 20 percent by weight that is water-soluble in combination with the co-solubilizing agent and the solution is buffered to a pH less than about 6. Methods for preparing the aqueous caffeine solutions of the present invention are also disclosed.

28 Claims, No Drawings

AQUEOUS CAFFEINE DOSAGE FORMS

BACKGROUND OF THE INVENTION

The present invention relates to caffeine dosage forms prepared as aqueous solutions of high levels of caffeine buffered to a pH at which the taste of the caffeine can be effectively masked. In particular, the present invention relates to the use of niacinamide and nicotinic acid as caffeine co-solubilizing agents to provide high concentration caffeine solutions with improved taste that are capable of being effectively formulated with taste-masking components. The present invention also relates to methods for making the buffered caffeine solutions.

Oral caffeine dosage forms are desirable for use as over-the-counter stimulants that can be prepared in the form of breath sprays or breath drops. As a central nervous system stimulant, the administration of caffeine in combination with analgesics and topical anesthetics increases the analgesic or anesthetic effect. Therefore, aqueous oral dosage forms of caffeine with these ingredients would be desirable to provide a product for the temporary relief of toothache or gum inflammation until a dental professional could be consulted.

Caffeine, however, has limited water solubility. This is evident from U.S. Pat. No. 5,382,436, which discloses topical caffeine compositions for use in the treatment of Herpes virus infections. From 8 to 12 percent by weight of caffeine is applied in the form of a dispersion in a topical excipient. This is but one known end-use application for which aqueous caffeine solutions of higher concentration would be desirable.

The acid addition salts of caffeine with citric or hydrochloric acid have significantly greater water solubility. However, the acid addition salts also have an unpleasant taste that is virtually impossible to mask in a commercially practical manner.

Unpleasant tastes are ordinarily masked with an artificial sweetener such as aspartame in combination with flavoring agents. However, solutions of caffeine hydrochloride and caffeine citrate at dosage-effective concentrations have pH's far too low, typically 2.0 and lower. The solutions cannot even be buffered for compounding with aspartame and flavoring agents, which are hydrolytically unstable at these pH's and degrade to reveal the unpleasant taste of the caffeine acid addition salt solution.

There exists a need for higher concentration caffeine solutions in water at pH's acceptable for formulation with taste-masking ingredients.

SUMMARY OF THE INVENTION

This need is met by the present invention. It has now been discovered that caffeine can be co-solubilized with niacinamide and nicotinic acid to form caffeine solutions at dosage-effective concentrations with pH's that can be buffered to a pH at which the taste of the caffeine can be effectively masked. For taste masking to be effective, the pH must be buffered to a pH less than about 6, and preferably less than about 5. For example, the optimum pH for the use of aspartame as a taste-masking agent is about 4.3.

Therefore, in accordance with one embodiment of the present invention, an aqueous caffeine solution is provided containing a co-solubilizing agent selected from niacinamide, nicotinic acid and mixtures thereof present at a level up to the maximum concentration soluble in water and in a weight ratio to caffeine less than 1.50:1, wherein the caffeine present up to the maximum level between about 2 and about 20 percent by weight that is water-soluble in combination with the co-solubilizing agent, and the solution is buffered to a pH less than about 6.

A pH less than about 5 is preferred, with a pH of about 4.3 being more preferred.

Unexpectedly, folic acid has been found to have significantly increased water-solubility in the caffeine solutions of the present invention. This is desirable, because caffeine is believed to deplete folic acid, an essential B-vitamin, in the body. Therefore, preferred caffeine solutions of the present invention further include folic acid at a level up to the maximum concentration soluble in the caffeine solution. Preferably, the folic acid is present at a level soluble in the caffeine solution up to the amount effective to provide the minimum Recommended Daily Allowance (RDA) of folic acid in a 4.0 mL quantity of the caffeine solution.

Preferred caffeine solutions in accordance with the present invention are also fortified with other essential vitamins, minerals and health food additives. This will influence the choice of a buffering system. Vitamin C, ascorbic acid, is a strong acid that when present at the 50 percent minimum RDA will reduce the pH of caffeine solutions in accordance with the present invention below 4.3. Buffering with a basic system based on sodium bicarbonate, sodium hydroxide, and the like, is necessary. Otherwise, solutions based on caffeine with niacinamide and nicotinic acid and folic acid will produce a pH above 6.0 that requires buffering with an acidulent, preferably one generally regarded as safe, such as citric acid, hydrochloric acid, acetic acid and the like. Nicotinic acid or ascorbic acid may also be used as the acidulent.

Caffeine solutions in accordance with the present invention may also include an analgesic that is capable of being effectively absorbed through the skin or mucous membrane, such as acetylsalicylic acid, acetaminophen, ibuprofen, ketoprofen, menthol and the like. The caffeine solutions of the present invention have unexpectedly been found to promote the water-solubility and effect of topical anesthetics capable of being absorbed through the skin and mucous membranes such as procaine, benzocaine, lidocaine and the like. Therefore, caffeine solutions in accordance with the present invention may further optionally include an analgesic or topical anesthetic capable of being absorbed through the skin or mucous membrane.

The present invention also provides methods by which the aqueous caffeine solutions of the present invention may be prepared. In accordance with this embodiment of the present invention, a method is provided for preparing an aqueous caffeine solution including the steps of:

dissolving caffeine and a co-solubilizing agent selected from niacinamide, nicotinic acid and mixtures thereof in water, so that an aqueous solution of caffeine is formed, wherein the co-solubilizing agent is present at a level up to the maximum concentration soluble in water and in a weight ratio relative to caffeine less than 1.50:1, and the caffeine is present up to the maximum level between about 2 and about 20 percent by weight that is water-soluble in combination with the co-solubilizing agent; and buffering the caffeine solution to a pH less than about 6.

Without being bound by any particular theory, it is believed that the niacinamide and nicotinic acid function as a combination co-solubilizing agent that promotes the hydration of the caffeine in water. At higher concentrations, these ingredients may also form water-soluble acid addition salts with the caffeine. Regardless, the co-solubilizing agents effectively provide aqueous caffeine solutions at concentrations greater than 2 percent by weight at a pH that is capable of being buffered to a level at which the taste of the caffeine solution may be effectively masked with artificial flavors and sweeteners. The co-solubilizing agents also provide aqueous caffeine solutions with improved taste compared to the aqueous caffeine addition salt solutions of the prior art, making it simpler to mask the taste of the aqueous caffeine solutions of the present invention.

DETAILED DESCRIPTION OF THE PREFERRED EMBODIMENT

The aqueous caffeine solutions of the present invention contain caffeine at a level between about 2 and about 20 percent by weight. Aqueous solutions of caffeine up to about 2 percent by weight can be readily prepared without a co-solubilizing agent. For amounts greater than about 2 percent, the level of caffeine employed in the solutions of the present invention will depend upon the co-solubilizing agent selected.

Niacinamide will co-solubilize caffeine solutions up to about 20 percent by weight of caffeine. The amount of niacinamide employed will range in a weight ratio to caffeine between about 0.25 and about 1.50:1, depending upon the amount of caffeine present. That is, caffeine levels just above 2 percent by weight can be solubilized with about a 0.25:1 weight ratio of niacinamide to caffeine. However, as the level of caffeine increases, the requisite weight ratio of niacinamide to caffeine also increases up to a level of about 1.50:1 for caffeine levels of about 20 percent by weight. The weight ratios of niacinamide effective for selected concentrations of caffeine are depicted below in Table I:

TABLE I

| CAFFEINE WEIGHT PERCENT | WEIGHT RATIO NIACINAMIDE:CAFFEINE |
|---|---|
| 2.5% | 4:10–5:10 |
| 5.0% | 7.5:10–8.5:10 |
| 7.5% | 9.0:10–1.0:1.0 |
| 10.0% | 1:1 |
| 12.5% | 1.1:1.0–1.2:1.0 |
| 15.0% | 1.2:1.0–1.25:1.0 |
| 17.5% | 1.25:1.0–1.35:1 |
| 20.0% | 1.35:1.0–1.45:1.0 |

Of course, greater levels of niacinamide can be employed up to a weight ratio t caffeine of 1.50:1. Preferred solutions have a level of caffeine between about 2.5 and about 5.0 percent by weight and a weight ratio of niacinamide to caffeine between about 0.40 and about 0.90: 1. Even more preferred solutions contain a level of caffeine between about 2.75 and about 3.50 percent by weight and a weight ratio of niacinamide to caffeine of about 0.60:1.

The limited water solubility of nicotinic acid correspondingly reduces the amount of caffeine that can be solubilized with this co-solubilizer. Nicotinic acid can be dissolved in water up to a level of about 1.67 percent by weight. The maximum concentration can solubilize up to about 2.30 percent by weight of caffeine at pH 4.0.

Increasing the pH with an alkalizing agent increases the amount of nicotinic acid that can go into solution, which consequently increases the amount of caffeine that can be solubilized. Greater than 6 percent by weight of nicotinic acid in solution requires a pH greater than desired levels. In addition, at higher concentrations, nicotinic acid is an undesirable rubifacient.

The caffeine solutions of the present invention are buffered to a pH less than about 6, and preferably less than about 5. Solutions containing aspartame are preferably buffered to a pH of about 4.3. The solutions may contain a mixture of niacinamide and nicotinic acid.

The buffering agent selected will depend upon the solution pH produced by the other ingredients. For solutions containing only caffeine, a co-solubilizing agent and optionally folic acid, a pH above 6 may result, that can be buffered below 6 with an acidulent such as citric acid, nicotinic acid, hydrochloric acid, ascorbic acid and the like. The preferred acidulents are nicotinic acid, citric acid and ascorbic acid. When strongly acidic ingredients such as ascorbic acid are used, a basic buffer may be needed. For example, when ascorbic acid is present at a level greater than about 1.30 percent by weight, a solution pH less than about 4.0 will result, necessitating the addition of a basic buffer such as sodium bicarbonate, sodium hydroxide, potassium hydroxide, potassium carbonate and the like. Essentially any alkalizing agent may be employed. Sodium hydroxide is the preferred basic buffer.

The amount of buffer employed should be that amount effective to produce the desired pH. That is, an amount effective to produce a pH less than about 6, and preferably an amount effective to produce a pH less than about 5. Solutions of the present invention buffered with citric acid will typically contain between about 0.10 and about 1.0 percent by weight of citric acid.

Preferred solutions in accordance with the present invention also contain folic acid to replace amounts of this essential B-vitamin believed to be depleted by caffeine. As noted above, the present invention incorporates the unexpected discovery that the caffeine solutions of the present invention increase the solubility of folic acid in water. Therefore, caffeine solutions in accordance with the present invention preferably contain the maximum amount of folic acid soluble therein, up to an amount effective to provide at least 50 percent of the minimum RDA of folic acid in a 4.0 mL quantity of caffeine solution.

The caffeine solutions of the present invention may optionally include other essential vitamins in the maximum quantity soluble up to an amount effective to provide the minimum RDA in a 2.5 mL quantity of solution. Such vitamins include ascorbic acid, A, D and E Vitamins, pyridoxine and thiamine and acid addition salts thereof, where applicable. Anti-allergens and stimulants may also be included, such as ginseng, epinephrine, ephedrine, pseudoephedrine, norephedrine, norepinephrine, and the like, and acid addition salts thereof. Dextromethorphan acid addition salts may also be included.

Ascorbic acid may also be employed as a buffer. However, the amount required to buffer a caffeine/niacinamide solution has little nutritional value, because of the strong acidity of ascorbic acid. When nutritional quantities of ascorbic acid are employed, it becomes necessary to buffer the solution with a basic buffer system.

The caffeine solutions of the present invention may contain an artificial sweetener and natural or artificial flavorings and agents to mask the taste of the caffeine, co-solubilizing agent and other ingredients. The artificial sweeteners to be used in the caffeine solutions of the invention can be any of those known for use in food products. Examples include saccharin, cyclamate, acesulfame K, aspartame, alatame, and the like. The artificial sweetener will be present at a level between about 0.10 and about 2.0 percent by weight. The preferred artificial sweetener is aspartame at a level of between about 0.10 and about 1.0 percent by weight, and preferably at a level of about 1.0 percent by weight. One of ordinary skill in the art will appreciate that significant quantities of potent artificial sweeteners are being employed, thus illustrating the difficulties inherent in masking the taste of caffeine solutions.

Examples of suitable natural and artificial flavoring agents include vanillin, wintergreen, peppermint oil, orange oil, lemon oil, licorice, sassafras, natural and artificial cherry, natural vanilla extract, ethylene vanillin, coffee extract, chocolate extract, artificial chocolate flavoring, cocoa extract, and the like. The flavoring agents are typically oils that must be solubilized in the caffeine solutions of the present invention with an emulsifying system. Typically, a stock solution of flavoring agent oil in an emulsifier system is prepared that is then dispersed in the caffeine solutions of the present invention. Flavoring agent oils are preferably dissolved in a 50:50 blend of Tween 20 and Tween 80 at levels between about 10 and about 25 percent by weight, and preferably at a level of about 20 percent by weight. Between about 0.25 and about 10.0 percent by weight, and preferably between about 0.50 and about 1.50 percent by weight of this stock solution is then added to the caffeine solutions of the present invention. At higher concentrations of caffeine and the co-solubilizing agent, an amount of emulsifier at the lower end of the disclosed range is effective.

The caffeine solutions of the present invention may optionally further include an effective amount of an analgesic capable of being topically absorbed through the skin or mucous membranes or an effective amount of a topical anesthetic capable of being absorbed through the skin or mucous membranes. Examples of suitable analgesics include acetyl salicylic acid, acetaminophen, ibuprofen, ketoprofen, menthol and the like. Such analgesics have been found to have increased water solubility in the caffeine solutions of the present invention. Thus, for example, solutions in accordance with the present invention containing a topically absorbed analgesic may include acetyl salicylic acid, i.e., aspirin, at levels up to about 10.0 percent by weight.

Topical anesthetics suitable for use with the present invention include procaine, lidocaine, benzocaine, holocaine, dibucaine, acid addition salts thereof, and the like. The topical anesthetics, especially the acid addition salts, have also been found to have increased water solubility in the caffeine solutions of the present invention. Thus, solutions in accordance with of the present invention containing a topical anesthetic may, for example, include procaine hyddrochloride at levels up to about 10.0 percent by weight. The caffeine solutions of the present invention optionally containing an analgesic or topical anesthetic are effective in the temporary relief of skin or mucous membrane inflammation, such as is associated with toothache, gum disease, Herpes infection, sore throat and the like.

The caffeine solutions of the present invention are prepared by dissolving the desired amount of caffeine, co-solubilizing agent, and the water-soluble optional ingredients such as folic acid, other vitamins and minerals, analgesic, topical anesthetic, etc., in water with stirring. Room temperature water may be employed, or the water may be heated to a temperature up to about 100° C. to facilitate the dissolution of the ingredients.

The pH of the solution is measured and adjusted to the desired pH with an appropriate buffering agent. That is, an acidic buffering agent is used if the pH is high and is to be decreased, while a basic buffering agent is used if the pH is low and is to be increased. Once the pH of the caffeine solution is adjusted, the emulsifier system containing the water-insoluble ingredients is added. Typically, this is a 50:50 blend of Tween 20 and Tween 80 containing the flavoring agent oils.

After the pH is adjusted, and either before, during or after the flavoring agent oil-emulsifier system is added, the artificial sweetener may be added. Folic acid, when employed, must be added first, in the form of an alkali salt. The mixture is then stirred until a uniform, homogeneous solution is obtained. The resulting solution is then dispensed into containers by conventional means.

The caffeine solutions of the present invention are preferably administered in the form of a breath spray or breath drops delivering about a 2.5 to 4.0 mL quantity of solution. However, the caffeine solutions of the present invention may also be administered in the form of liquicaps, gum, candy such as lozenges or dark, milk or white chocolate-based candy.

Thus, it can be appreciated that the present invention provides a concentrated oral caffeine dosage form without the objectionable taste heretofore associated with concentrated caffeine solutions. The following examples further illustrate the present invention, and are not to be construed as limiting the scope thereof. All parts and percentages are by weight unless expressly indicated to be otherwise, and all temperatures are in degrees Celsius. All chemicals were obtained from Amend Drug & Chemical of Irvington, N.J.

EXAMPLES

Example 1

To 500 g of water was added with mixing 16 g caffeine, 9.8 g niacinamide and 20 mg folic acid. The ingredients dissolved rapidly, forming a uniform, homogeneous solution. The pH of the solution was adjusted to 4.3 with 0.7 g citric acid. 8.3 g of a mixture of 20 percent by weight of peppermint oil, 40 percent by weight of Tween 20 and 40 percent by weight of Tween 80 is then added to the solution with stirring, followed by 3.5 g aspartame and 1 mg of vanillin.

Stirring was continued until a uniform, homogeneous minty vanilla-flavored caffeine solution was obtained.

Example 2

A caffeine solution was prepared as in Example 1 using 22 g niacinamide, 22 g caffeine, 40 mg folic acid and 8 g ascorbic acid. The same quantities of the flavoring agent oil emulsifier system, aspartame, vanillin and water were employed. The folic acid was added in the form of a 1 percent aqueous solution buffered to a pH greater than 10, with about 10 percent by weight of sodium hydroxide. Because of the acidity of the ascorbic acid, the pH of the solution was adjusted to 4.3 with 1.5 g of sodium hydroxide.

Example 3

A caffeine solution was prepared as in Example 1 using 8 g niacinamide, 16.1 g caffeine, 1 g nicotinic acid, 8.8 g of the 1 percent folic acid mixture of Example 2, 5.4 g aspartame and 5.4 g of peppermint oil, emulsified as in Example 1. 500 g of water was employed. A minty-flavored solution was obtained containing 3.0 percent by weight of caffeine at a pH of 4.5.

Example 4

A caffeine solution was prepared as in Example 1 based on 82.8 g of water, to which was added 1.8 g nicotinic acid, 3.0 g caffeine, 0.8 g of the 1 percent folic acid solution of Example 2, 1.6 g ascorbic acid, 1.0 g aspartame and 8.8 g of a flavoring agent oil emulsified as in Example 1, but substituting orange oil for peppermint oil. Because of the acidity of the ascorbic acid, the pH of the solution was adjusted to 4.5 with 0.2 g of sodium hydroxide. An orange-flavored solution containing 3.0 percent by weight of caffeine was obtained.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A caffeine oral dosage form comprising: an aqueous solution of between
   about 2 and about 20 percent by weight of caffeine; niacinamide present in a weight ratio to said caffeine of between about 0.25:1 and about 1.50:1; a buffering agent present in an amount effective to buffer said solution to a pH of between about 4 and about 6; and an amount of an artificial sweetener effective to mask the taste of the caffeine.

2. The caffeine oral dosage form of claim 1, which is buffered to a pH less than about 5.

3. The caffeine oral dosage form of claim 2, which is buffered to a pH of about 4.3.

4. The caffeine oral dosage form of claim 1, wherein said buffering agent is an acidulent selected from the group consisting of citric acid, ascorbic acid and hydrochloric acid.

5. The caffeine oral dosage form of claim 1, wherein said buffering agent is an alkalizing agent selected from the group consisting of sodium hydroxide, sodium bicarbonate, potassium hydroxide and potassium bicarbonate.

6. The caffeine solution of claim 1, further comprising one or more essential vitamins other than niacinamide or nicotinic acid at a level soluble in said aqueous solution up to an amount effective to provide the minimum Recommended Daily Allowance of said vitamin in a 4.0 mL quantity of said aqueous solution.

7. The caffeine oral dosage form of claim 6, wherein said vitamin is selected from the group consisting of ascorbic acid, folic acid, an A vitamin, a D vitamin, an E vitamin, pyridoxine and thiamine.

8. The caffeine oral dosage form of claim 1, further comprising an effective amount of an analgesic, topical anesthetic anti-allergen or stimulant capable of being effectively absorbed through the skin or mucus membrane.

9. The caffeine oral dosage form of claim 8, comprising an analgesic selected from the group consisting of acetyl salicylic acid, acetaminophen, ibuprofen, ketoprofen and menthol.

10. The caffeine oral dosage form of claim 8, comprising a topical anesthetic selected from the group consisting of procaine, lidocaine, benzocaine, holocaine and dibucaine or an acid addition salt thereof.

11. The caffeine oral dosage form of claim 8, comprising an anti-allergen or stimulant selected from the group consisting of ginseng, epinephrine, ephedrine, pseudoephedrine, norephedrine and norepinephrine or an acid addition salt thereof.

12. The caffeine oral dosage form of claim 1, wherein said artificial sweetener is aspartame at an amount of between about 0.10 and about 1.0 percent by weight.

13. The caffeine oral dosage form of claim 1 further comprises one or more natural or artificial flavoring agents selected of the group consisting of vanillin, wintergreen, peppermint oil, orange oil, lemon oil, licorice, sassafras, natural and artificial cherry flavor, natural vanilla extract, ethylene vanillin, coffee extract, chocolate extract, artificial chocolate flavoring and cocoa extract.

14. A caffeine oral dosage form comprising, an aqueous solution of between about 2 and about 20 percent by weight of caffeine; nicotinic acid present in a weight ratio to said caffeine between about 0.25:1 and about 1.50:1; an alkaline buffering agent in an amount effective to both buffer said solution to a pH of between about 4 and about 6 and to facilitate taste marking; and an artificial sweetener effective to mask the taste of the caffeine.

15. The oral dosage form of claim 14, which is buffered to a pH less than about 5.

16. The oral dosage form of claim 15, which is buffered to a pH of about 4.3.

17. The oral dosage form of claim 14, wherein said nicotinic acid is present at a level up to about 1.67 percent by weight and said caffeine is present at a level up to about 2.30 percent by weight.

18. The oral dosage form of claim 14, wherein said alkaline buffering agent is selected from the group consisting of sodium hydroxide, sodium bicarbonate, potassium hydroxide and potassium bicarbonate.

19. The oral dosage form of claim 14, further comprising one or more essential vitamins at a level soluble in said aqueous solution up to about an amount effective to provide the minimum Recommended Daily Allowance of said vitamin in a 4.0 mL quantity of said aqueous solution.

20. The oral dosage form of claim 19, wherein said vitamin is selected from the group consisting of ascorbic acid, folic acid, and A vitamin, a D vitamin, an E vitamin, pyridoxine and thiamine.

21. The oral dosage form of claim 19, further comprising an effective amount of an analgesic, topical anesthetic, anti-allergen or stimulant capable of being effective absorbed through the skin or mucous membrane.

22. The oral dosage form of claim 21, comprising an analgesic selected from the group consisting of acetyl salicylic acid, acetaminophen, ibuprofen, ketoprofen and menthol.

23. The oral dosage form of claim 21, comprising a topical anesthetic selected from the group consisting of procaine, lidocaine, benzocaine, holocaine and dibucaine or an acid addition salt thereof.

24. The oral dosage form of claim 21, comprising an anti-allergen or stimulant selected from the group consisting of ginseng, epinephrine, ephedrine, pseudoephedrine, norephedrine and norepinephrine, or the acid addition salt thereof.

25. The oral dosage form of claim 14, wherein said artificial sweetener is selected from the group consisting of saccharine, cyclamate, acesulfame K, aspartame and alatame.

26. The oral dosage form of claim 25, wherein said artificial sweetener is aspartame at a level of between about 0.10 and about 1.0 percent by weight.

27. The caffeine solution of claim 14, further comprising one or more natural or artificial flavoring agents selected from the group consisting of vanillin, wintergreen peppermint oil, orange oil, lemon oil, licorice, sassafras, natural and artificial cherry flavor, natural vanilla extract, ethylene vanillin, coffee extract, chocolate extract, artificial chocolate flavoring and cocoa extract.

28. The oral dosage form of claim 1, wherein said artificial sweetener is selected from the group consisting of saccharine, cyclamate, acesulfame K, aspartame and alatame.

* * * * *

UNITED STATES PATENT AND TRADEMARK OFFICE
CERTIFICATE OF CORRECTION

PATENT NO. : 5,900,416
DATED : May 4, 1999
INVENTOR(S) : Markson

It is certified that error appears in the above-identified patent and that said Letters Patent is hereby corrected as shown below:

Column 3, line 47, "t" should read --to--.

Column 5, line 10, "that is" should read --and--.

Column 5, line 39, delete "of".

Column 7, line 26, "solution" should read --oral dosage form--.

Column 7, line 57, "of" should read --from--.

Column 8, line 26, "and" should read --an.--.

Column 8, line 28, "19" should read --14--.

Column 8, line 30, "effective" should read --effectively--.

Column 8, line 42, "the" should read --an--.

Signed and Sealed this

Fourteenth Day of September, 1999

Attest: -

Q. TODD DICKINSON

*Attesting Officer*   *Acting Commissioner of Patents and Trademarks*